United States Patent
Swanson et al.

(10) Patent No.: US 6,914,960 B2
(45) Date of Patent: Jul. 5, 2005

(54) MINIATURE X-RAY EMITTER HAVING INDEPENDENT CURRENT AND VOLTAGE CONTROL

(75) Inventors: Vance Swanson, Santa Rosa, CA (US); Zirao Zheng, Santa Rosa, CA (US); Victor I. Chornenky, Minnetonka, MN (US); Eunsung Park, Minneapolis, MN (US); Matthew Rust, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 124 days.

(21) Appl. No.: 10/427,349

(22) Filed: Apr. 30, 2003

(65) Prior Publication Data

US 2004/0218720 A1 Nov. 4, 2004

(51) Int. Cl.$^7$ ............................................... H01J 35/00
(52) U.S. Cl. ........................................ 378/119; 378/136
(58) Field of Search ........................ 378/64, 65, 68, 378/119, 121, 136; 604/20

(56) References Cited

U.S. PATENT DOCUMENTS

| 5,428,658 A | 6/1995 | Oettinger et al. ........... 378/119 |
| 6,319,188 B1 | 11/2001 | Lovoi ............................ 600/3 |
| 6,463,124 B1 * | 10/2002 | Weisman et al. ........... 378/136 |

* cited by examiner

Primary Examiner—Edward J. Glick
Assistant Examiner—Courtney Thomas

(57) ABSTRACT

An apparatus for emitting x-rays comprises a housing which contains an anode having an electron receiving surface and a cathode having an electron emitting surface. A cable couples the anode to a source of high voltage. An optical fiber secured to the cable has a proximal end coupled to a source of optical energy and a distal end configured to direct the optical energy onto the cathode's electron emitting surface. The cathode emits electrons which strike the anode to create x-ray radiation.

9 Claims, 2 Drawing Sheets

US 6,914,960 B2

MINIATURE X-RAY EMITTER HAVING INDEPENDENT CURRENT AND VOLTAGE CONTROL

TECHNICAL FIELD

This invention relates generally to a miniature x-ray apparatus, and more particularly to an x-ray emitter configured to permit independent control of the operating voltage and current.

BACKGROUND OF THE INVENTION

The medical community is constantly striving for less invasive techniques for treating patients. To this end, miniature x-ray emitters have been developed and have become an integral part of a variety of treatment protocols.

For example, in the case of coronary artery disease, balloon angioplasty or percutaneous transluminal angioplasty has become relatively common. In a large number of cases, however, restinosis occurs at the site where the angioplasty was administered. Restinosis is the re-narrowing or reclosing of the treated coronary artery and is largely related to the development of neo-intimal hyperplasia that occurs within an artery after it has been treated with a balloon or atherectomy device. In a sense, restinosis is scar tissue that forms in response to a mechanical intervention within a vascular structure. This scarring of the vessel can be so severe that blood flow through the vessel is obstructed. One known form of countermeasure involves the use of stents. A stent is a metal, generally tubular, vascular prosthesis which is implanted after angioplasty to mechanically hold the vessel lumen open. However, even with a stent in place, in-stent restinosis still tends to occur in a large percentage of cases.

To prevent or limit restinosis, drugs such as Heparin, Dexamethasome, Integralin, and others have been utilized. These drugs generally include anticoagulants and arterial smooth muscle proliferation inhibitors as well agents to prevent the aggregation of platelets.

It is also known that radiation is effective in reducing restinosis after angioplasty. In the past, radiation was administered by mounting a radioactive isotope on the tip of a catheter and inserting the catheter into a vessel until the emitter reaches a lesion location. The radioactive isotope would then emit gamma or beta radiation to treat the lesion. Unfortunately, the use of such radioactive isotopes requires protective shielding and special care in handling and disposal. Furthermore, such techniques result in irradiation throughout the length of the blood vessel although it is only necessary that a particular location be irradiated. Also, the depth of irradiation is difficult to control when utilizing such techniques thus presenting a further disadvantage.

More recently, x-ray devices have been developed which are capable of delivering radiation to remote locations in the body, including narrow passageways as small as blood vessels. Such devices include radiation emitters which can be switched on and off and do not require the use or handling of radioactive isotopes. For example, U.S. Pat. No. 5,428,658 entitled "X-ray Source With Flexible Probe" issued on Jun. 27, 1995, describes an x-ray emitter utilizing fiber optic cables. The fiber optic cables are designed to carry light waves which activate a photocathode in the emitter. The x-ray emitter is positioned at the distal end of a high voltage cable which is designed as an optical fiber 2–3 millimeters in diameter with a metal central core which carries the high voltage. The optical fiber is also utilized to transmit light pulses from a laser at the proximal end of the fiber to an electron emissive surface at the distal end. The electrons emitted from the surface generate an electric current in the high voltage gap of the x-ray unit resulting in x-ray emission.

A similar arrangement is shown and described in U.S. Pat. No. 6,319,188 entitled "Vascular X-Ray Probe" issued Nov. 20, 2001. In this case, an x-ray probe is formed at an optical fiber cable with a high voltage conductor embedded in the optical fiber. The optical fiber has an external ground coating and feeds power to a small x-ray emitter at the end of the cable. The optical fiber provides a conduit for optical irradiation, preferably in the form a laser beam, which is fed to a thermionic cathode mounted at the end of the light path. The laser beam heats the cathode causing it to emit electrons. An anode or target is positioned opposite the cathode within a vacuum chamber, and a ground lead is fed to the anode via an external coating over the emitter.

Devices of the type described above in the referenced patents have the ability to independently control both the operating voltage and the current thus allowing for independent control of depth of penetration of irradiation into tissue and the power generated by the source; however, the fact that in such devices the optical fiber for transmission of light radiation and the high voltage cable for the power supply are combined renders both suboptimal. The high voltage cable, which is made of a thick optical fiber, is generally not flexible enough to be applied as a catheter source similar to Iridium 192 source used in afterloaders for brachytherapy. The optical guide has high losses, and because light exits from the distal end of the fiber into the vacuum chamber in the area of a high electric field, it compromises the high voltage holdoff of the unit.

Therefore, it should be appreciated that it would be desirable to provide an x-ray emitter and apparatus that provides for the independent control of the operating voltage and current while at the same time offering the advantages of flexibility. A flexible catheter source of ionizing irradiation would be suitable for intraoperative radiation brachytherapy.

SUMMARY OF THE INVENTION

According to a first aspect of the invention there is provided an apparatus for emitting x-rays comprising a housing which contains an anode having an electron receiving surface and a cathode having an electron emitting surface. A cable couples the anode to a source of high voltage. An optical fiber secured to the cable has a proximal end coupled to a source of optical energy and a distal end configured to direct the optical energy onto the cathode's electron emitting surface. The cathode emits electrons which strike the anode to create x-ray radiation.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like reference numerals denote like elements, and.

DETAILED DESCRIPTION OF THE EXEMPLARY EMBODIMENT

The following description is exemplary in nature and is not intended to limit the scope, applicability, or configuration of the invention in any way. Rather, the following description provides a convenient illustration for implementing exemplary embodiments of the invention. Various changes to the described embodiments may be made in the function and arrangement of the elements described herein without departing from the scope of the invention.

Figure 1:
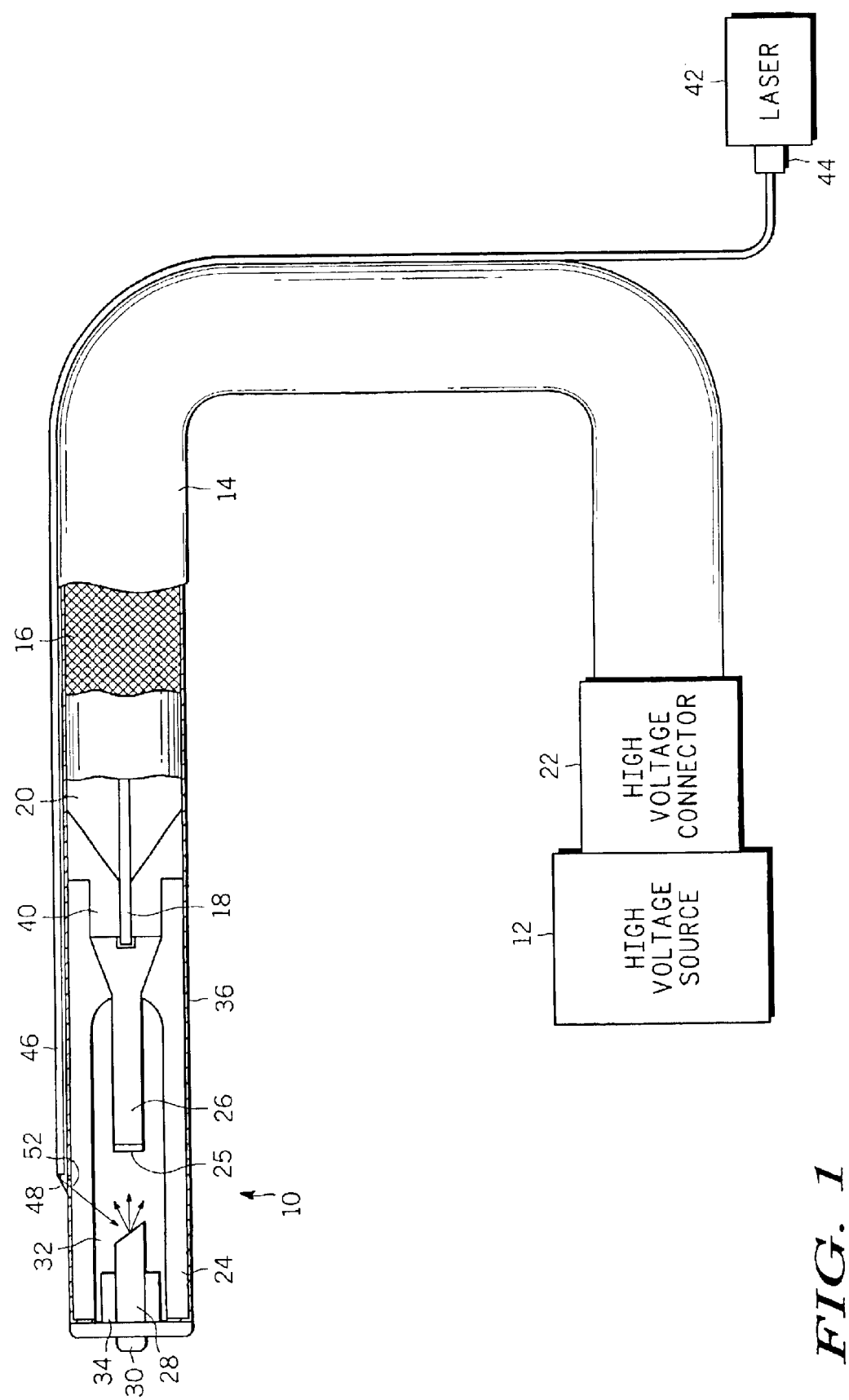
FIG. 1 is a diagrammatic illustration, partially in cross-section, of a miniature x-ray apparatus in accordance with the present invention.
Figure 2:
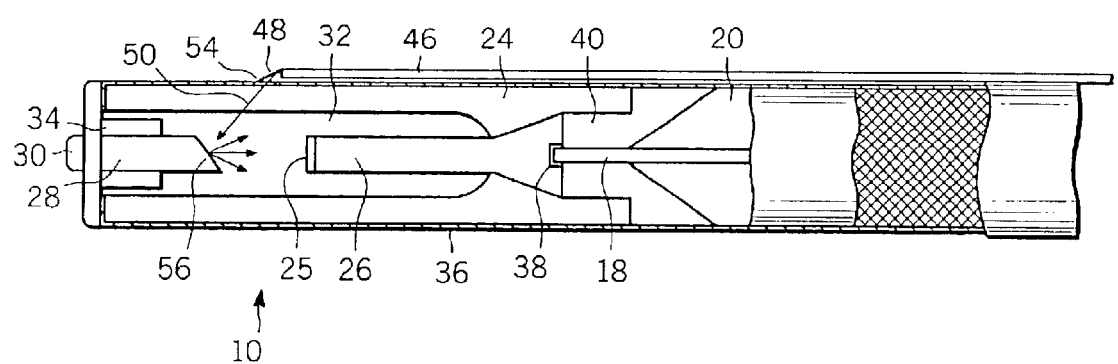
FIG. 2 an exploded cross-sectional view of the distal end of the miniature x-ray apparatus shown in FIG. 1.

A miniature x-ray emitter in accordance with the present invention is shown partially in cross-section in FIGS. 1 and 2. It comprises an x-ray emitter 10, a high voltage source 12, and a cable 14 for coupling high voltage source 12 to emitter 10. High voltage cable 14 may comprise a coaxial cable having a braid 16, a center conductor 18, and an insulating layer 20 separating braid 16 from center conductor 18. Cable 14 is connected to high voltage source 12 by means of a high voltage connector 22.

Emitter 10 comprises a housing 24 (for example made of quartz) which surrounds an anode 26 (e.g. gold, tungsten, etc.) and a photosensitive cathode 28. An end cap 30 (e.g. molybdenum) is secured to the distal end of housing 24 as, for example, by brazing. Housing 24, anode 26, cathode 28, and end cap 30 define a vacuum chamber 32. The vacuum in vacuum chamber 32 is maintained by a getter 34; e.g., a non-evaporable getter of the type provided by, for example, SAES located in Colorado Springs, Colo. Braid 16 of coaxial cable 14 is electrically coupled to a metal coating 36 (e.g. titanium-silver) disposed on housing 24, and center conductor 18 of cable 14 is electrically coupled to anode 26 as is shown at 38. An insulating compound 40 (e.g. an ultra-violet cured epoxy) is provided in the space defined by housing 24, anode 26 and the distal end of cable 14 so as to prevent electrical breakdown from occurring in the connection area.

A laser 42 is coupled to the proximal end of a multimode optical fiber 46 by means of a fiber optic connector 44. Optical fiber 44 is provided with a plastic jacket (not shown), and is secured (e.g. adhesively) on coaxial cable 14. To enhance flexibility, optical fiber 44 may alternatively follow a helical path along and around high voltage cable 14. The distal end of optical fiber 46 is coupled to a microprism 48 which deflects a laser beam indicated by arrow 50 through an opening 52 in metal coating 36 and onto surface 56 of cathode 28.

When the laser beam strikes electron emitting surface 56 of cathode 28, electrons are emitted from surface 56 into the vacuum gap between cathode 28 and anode 26 where the electrons are accelerated by the electric field and strike electron receiving surface 25 of anode 26 causing x-ray energy to be radiated in all directions. As can be seen, surface 56 is configured to be at an angle (e.g. 10–30 degrees) with the longitudinal axis of cathode 28 and anode 26 so as to facilitate the direct impingement of electrons emitted from surface 56 onto anode 26.

Thus, there has been provided a flexible miniature x-ray emitter which permits the independent control of the operating voltage and current. Such a device may be used as a brachytherapy radiation source and can be easily utilized in a standard operating room without the need for special protection from gamma radiation.

In the foregoing specification, the invention has been described with reference to specific embodiments. However, it should be appreciated that various modifications and changes can be made without departing from the scope of the invention as set forth in the appended claims. Accordingly, the specification and figures should be regarded as illustrative rather than restrictive, and all such modifications are intended to be included within the scope of the present invention.

What is claimed is:

1. An apparatus for emitting x-rays, comprising:
   a housing having an outer surface;
   a metallic coating on said outer surface;
   an anode disposed within said housing and having an electron receiving surface;
   a cathode disposed within said housing and having an electron emitting surface;
   a cable configured for coupling said anode to a source of high voltage; and
   an optical fiber secured to said cable, said optical fiber having a proximal end configured to receive optical energy and a distal end configured to direct optical energy onto said electron emitting surface thereby causing said cathode to emit electrons which strike said electron receiving surface creating x-ray radiation, wherein said optical fiber directs optical energy onto said electron emitting surface through an opening in said metallic coating.

2. An apparatus according to claim 1 further comprising an optical prism optically coupled to the distal end of said optical fiber.

3. An apparatus according to claim 2 wherein said electron emitting surface is angled toward said optical prism.

4. An apparatus according to claim 3 wherein said cable is a coaxial cable having a center conductor electrically coupled to said anode.

5. An apparatus according to claim 4 wherein said optical energy is a laser beam.

6. An apparatus according to claim 5 wherein said electron emitting surface is angled at an angle of between approximately 10–30 degrees.

7. An apparatus according to claim 6 wherein said metal coating is titanium—silver.

8. An apparatus according to claim 7 wherein said optical fiber is adhesively secured to said housing.

9. An apparatus according to claim 8 wherein said housing is quartz.

\* \* \* \* \*